United States Patent
Wang et al.

(10) Patent No.: US 12,205,344 B2
(45) Date of Patent: Jan. 21, 2025

(54) FUNDUS COLOR PHOTO IMAGE GRADING METHOD AND APPARATUS, COMPUTER DEVICE, AND STORAGE MEDIUM

(71) Applicant: PING AN TECHNOLOGY (SHENZHEN) CO., LTD., Guangdong (CN)

(72) Inventors: Guanzheng Wang, Guangdong (CN); Lilong Wang, Guangdong (CN)

(73) Assignee: PING AN TECHNOLOGY (SHENZHEN) CO., LTD., Guangdong (CN)

( * ) Notice: Subject to any disclaimer, the term of this patent is extended or adjusted under 35 U.S.C. 154(b) by 0 days.

(21) Appl. No.: 17/613,454

(22) PCT Filed: Sep. 27, 2020

(86) PCT No.: PCT/CN2020/118191
§ 371 (c)(1),
(2) Date: Nov. 22, 2021

(87) PCT Pub. No.: WO2021/174821
PCT Pub. Date: Sep. 10, 2021

(65) Prior Publication Data
US 2023/0154142 A1    May 18, 2023

(30) Foreign Application Priority Data
Aug. 7, 2020    (CN) .......................... 202010790150.2

(51) Int. Cl.
*G06V 10/56*    (2022.01)
*G06T 3/40*    (2024.01)
(Continued)

(52) U.S. Cl.
CPC ................ *G06V 10/56* (2022.01); *G06T 3/40* (2013.01); *G06T 5/50* (2013.01); *G06V 10/44* (2022.01);
(Continued)

(58) Field of Classification Search
CPC ........ G06V 10/56; G06V 10/44; G06V 10/82; G06T 3/40; G06T 5/50;
(Continued)

(56) References Cited

U.S. PATENT DOCUMENTS

2020/0160521 A1* 5/2020 Wang .................. G06V 40/193
2020/0187775 A1  6/2020 Oh et al.
(Continued)

FOREIGN PATENT DOCUMENTS

CN    108095683 A    6/2018
CN    109784148 A    5/2019
(Continued)

OTHER PUBLICATIONS

S. K. Yadav, S. Kumar, B. Kumar and R. Gupta, "Comparative analysis of fundus image enhancement in detection of diabetic retinopathy," 2016 IEEE Region 10 Humanitarian Technology Conference (R10-HTC), Agra, India, 2016, pp. 1-5, doi: 10.1109/R10-HTC.2016.7906814. (Year: 2016).*
(Continued)

*Primary Examiner* — Matthew C Bella
*Assistant Examiner* — Janice E. Vaz
(74) *Attorney, Agent, or Firm* — CANTOR COLBURN LLP (57) ABSTRACT

A fundus color photo image grading method and apparatus, a computer device, and a storage medium are provided. The method comprises: obtaining an original image, enhancing the original image, and obtaining a target image (S100); performing color processing on the original image and the
(Continued)

target image, and respectively obtaining a first processed image and a second processed image (S200); using a pre-trained grading model to perform processing on the first processed image and the second processed image, and obtaining a target grading result (S300). Multi-color space first and second processed images act as model inputs, and prediction is performed by means of fused features on a whole image scale to implement the classification and grading of common fundus color photo diseases, so as to automatically screen fundus color photos with pathological changes, achieve a pre-screening effect, and improve operational efficiency.

17 Claims, 5 Drawing Sheets

(51) Int. Cl.
  *G06T 5/50* (2006.01)
  *G06V 10/44* (2022.01)
  *G06V 10/82* (2022.01)
  *G16H 50/20* (2018.01)
(52) U.S. Cl.
  CPC ............ *G06V 10/82* (2022.01); *G16H 50/20* (2018.01); *G06T 2207/10024* (2013.01); *G06T 2207/20221* (2013.01)
(58) Field of Classification Search
  CPC . G06T 2207/10024; G06T 2207/20221; G06T 2207/20084; G06T 2207/30041; G06T 7/0012; G16H 50/20; G16H 30/40; G16H 30/20; G06F 18/24; G06N 3/045; G06N 3/08
  See application file for complete search history.

(56) References Cited

U.S. PATENT DOCUMENTS

2020/0356805 A1* 11/2020 Sun .......................... G06T 5/90
2021/0304069 A1* 9/2021 Tang ...................... G06N 20/00
2022/0414868 A1* 12/2022 Wang ..................... G06V 10/82

FOREIGN PATENT DOCUMENTS

CN    110796161 A    2/2020
CN    111481166 A    8/2020

OTHER PUBLICATIONS

M. Zhou, K. Jin, S. Wang, J. Ye and D. Qian, "Color Retinal Image Enhancement Based on Luminosity and Contrast Adjustment," in IEEE Transactions on Biomedical Engineering, vol. 65, No. 3, pp. 521-527, Mar. 2018, doi: 10.1109/TBME.2017.2700627. (Year: 2018).*
Li X, Shen X, Zhou Y, Wang X, Li TQ. Classification of breast cancer histopathological images using interleaved DenseNet with SENet (IDSNet). PLoS One. May 4, 2020;15(5):e0232127. doi: 10.1371/journal.pone.0232127. PMID: 32365142; PMCID: PMC7198071. (Year: 2020).*
English Translation of International Search Report for International Application No. PCT/CN2020/118191; Application Filing Date: Sep. 27, 2020; Date of Search: May 6, 2021, 2 pages.
International Search Report for International Application No. PCT/CN2020/118191; Application Filing Date: Sep. 27, 2020; Date of Search: May 6, 2021, 4 pages.
Written Opinion for International Application No. PCT/CN2020/118191; Application Filing Date: Sep. 27, 2020; Date of Search: May 6, 2021, 3 pages.

* cited by examiner

FUNDUS COLOR PHOTO IMAGE GRADING METHOD AND APPARATUS, COMPUTER DEVICE, AND STORAGE MEDIUM

CROSS-REFERENCE TO RELATED APPLICATIONS

The present application is a National Stage of PCT Application No. PCT/CN2020/118191 filed on Sep. 27, 2020, which claims priority of Chinese Patent Application No. 202010790150.2, filed with the Chinese Patent Office on Aug. 7, 2020 and entitled "FUNDUS COLOR PHOTO IMAGE GRADING METHOD AND APPARATUS, COMPUTER DEVICE, AND STORAGE MEDIUM", the contents each of which are incorporated herein by reference thereto in their entity.

TECHNICAL FIELD

The present application relates to the technical field of artificial intelligence, and particularly to a color fundus photo image grading method and apparatus, a computer device, and a storage medium.

BACKGROUND

A Fundus image contains various physiological structures such as blood vessels, optic discs, and macular regions, which are prone to pathological changes as we grow older. During a fundus examination, one of the most widely used and most important methods is to take a color fundus photo, a doctor can directly observe and analyze whether there is an abnormality in the fundus of a photographed person through a photographed color fundus retina photo of the photographed person. However, the current reading and diagnosis of the color fundus photo is highly dependent on the doctor's experience and the workload is relatively large.

The inventor found that the existing color fundus photo identification is to perform matching and identification based on a standard image, however, the color fundus photo image in actual clinic is not the standard image, so identification accuracy is relatively low. Further, there are some automatic fundus image identification and partition methods are used for specific diseases, such as identification of diabetic retinopathy based on diabetic retinopathy grading, however, it is not possible for the diabetic retinopathy grading to take grading of common pathologies such as aged macula degeneration etc. into consideration. Therefore, there is a demand of an image grading method that automatically screens out a color fundus photo provided with pathology from color fundus photo.

SUMMARY

Technical Problem

Objectives of the present application are to provide an image grading method and apparatus for grading color fundus photos, a computer device, and a storage medium, so as to solve problems in the art that the color fundus photo identification mostly relies on the experience of doctors, only some diseases can be automatically identified based on the color fundus photos, and there is a lack of an automatic color fundus photo screening method suitable for common diseases.

Technical Solutions grading method for grading color fundus photos, which includes:

obtaining an original image, and performing enhancement processing on the original image to obtain a target image;

performing color processing on the original image and the target image to obtain a first processed image and a second processed image respectively;

processing the first processed image and the second processed image by using a pre-trained grading model to obtain a target grading result.

In order to achieve the above objectives, the present application further provides an image grading apparatus for grading color fundus photos, which includes:

a first processing module configured to obtain an original image and perform enhancement processing on the original image to obtain a target image, a second processing module configured to perform color processing on the original image and the target image to obtain a first processed image and a second processed image respectively, an execution module configured to process the first processed image and the second processed image by using a pre-trained grading model to obtain a target grading result.

In order to achieve the above objectives, the present application further provides a computer device, comprising a memory, a processor and a computer program stored in the memory and capable of being executed on the processor, wherein the processor, when executing the computer program, implements following steps of an image grading method for grading color fundus photos:

obtaining an original image, and performing enhancement processing on the original image to obtain a target image;

performing color processing on the original image and the target image to obtain a first processed image and a second processed image respectively;

processing the first processed image and the second processed image by using a pre-trained grading model to obtain a target grading result.

In order to achieve the above objectives, the present application further provides a computer-readable storage medium, comprising a plurality of storage media, each of the storage media being stored a computer program thereon, wherein the computer programs stored on the plurality of storage media, when executed by a processor, implement following steps of an image grading method for grading color fundus photos together:

obtaining an original image, and performing enhancement processing on the original image to obtain a target image;

performing color processing on the original image and the target image to obtain a first processed image and a second processed image respectively;

processing the first processed image and the second processed image by using a pre-trained grading model to obtain a target grading result.

Beneficial Effects

The image grading method and apparatus for grading color fundus photos, computer device, and storage medium provided by the present application obtain the target image by performing enhancement processing on the original image, and then perform color space processing on the original image and the target image respectively to obtain the first processed image and the second processed image both provided with six channels (i.e., RGBHSV), and finally perform grading and prediction on the first processed image and the second processed image by using the trained grading model to obtain the target grading result. In this solution, the first processed image and the second processed image in the multi-color space are as input of the model, and then the classification and grading of common fundus diseases shown in the color photos are realized through performing prediction based on the fused features at a full-image scale, so as to solve the problems that the color fundus photo identification in the prior art mostly depends on the experience of doctors, that only some diseases can be automatically identified based on the color fundus photos, and that there is a lack of a method for automatically screening out color fundus photos suitable for common diseases.

EMBODIMENTS OF THE PRESENT APPLICATION

In order to make the objectives, technical solutions, and advantages of the present application more comprehensible, the present application will be further described in detail with reference to the accompanying drawings and embodiments. It should be understood that the specific embodiments described herein are only used to explain the present application, and are not used to limit the present application. Based on the embodiments in the present application, all other embodiments obtained by those of ordinary skill in the art without creative work shall fall within the protection scope of the present application.

The image grading method and apparatus for grading color fundus photos, computer device and readable storage medium provided in the present application are applicable to the technical field of artificial intelligence, and provide an image grading method for grading color fundus photos based on a first processing module, a second processing module and an execution module. In the present application, enhancement operations such as clipping, scaling, normalization, and a contrast algorithm are performed on an original image by using the first processing module to obtain an enhanced original image as a target image; and then spatial color processing are performed on the original image and the target image separately by using the second processing module, where the RGB-channel images are processed to obtain RGB-HSV images provided with six channels so as to obtain corresponding first processed image and second processed image respectively; and finally grading prediction is performed, by the execution module, on the first processed image and the second processed image through using a trained grading model to obtain a target grading result. Specifically, during the processing process, the execution module first uses a first convolutional network and a second convolutional network to perform grading prediction on the first processed image and the second processed image respectively, and then performs grading prediction after feature fusion is performed on the first processed image and the second processed image, and finally the grading results obtained by the above-mentioned grading predictions are fused to obtain the target grading result. In this solution, the first processed image and the second processed image in a multi-color space are used as inputs of the model, and the prediction is performed at a full image scale by using the fused features, thereby achieving classifying and grading of common fundus diseases shown in the color photos, and solving the problems in the art that the color fundus photo identification mostly relies on the experience of doctors, only some diseases can be automatically identified based on the color fundus photos, and there is a lack of an automatic color fundus photo screening method suitable for common diseases. Through the above grading model, the color fundus photo provided with pathology can be automatically screened out to achieve an effect of pre-screening, thereby improving work efficiency.

First Embodiment

Figure 1:
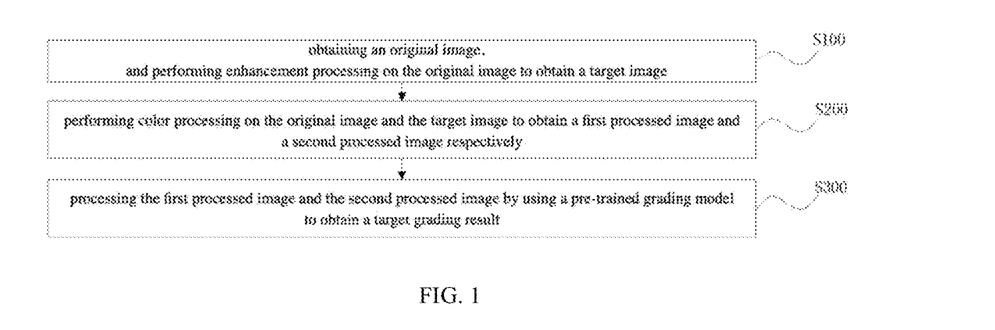
FIG. 1 is a flowchart of an image grading method for grading color fundus photos according to a first embodiment of the present application.

Please refer to FIG. 1, a image grading method for grading color fundus photos in this embodiment is applied to a server terminal, and is used to automatically screen out a color fundus photo provided with a disease in a color fundus photo identification scene of the medical field to achieve the effect of pre-screening. The present application may be applied to a smart medical scene to promote construction of a smart city, which includes following steps.

At S100, obtain an original image, and perform enhancement processing on the original image to obtain a target image.

In this implementation, sizes of the original images collected by different color fundus photography devices are different, and color distributions thereof are also quite different, therefore the original images need to be preprocessed (that is, the following steps from S110 to S130) first in order to ensure accuracy of a grading result. In this solution, the enhancement processing adopts a relatively common processing method, and other image enhancement methods used for color fundus photo identification in the prior art may also be applied herein.

Figure 2:
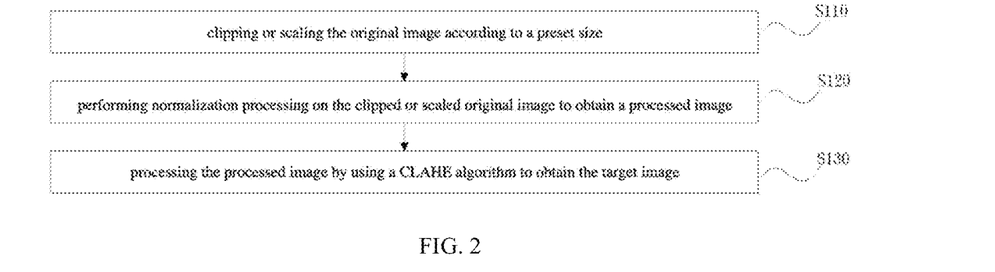
FIG. 2 is a flowchart of performing enhancement on an original image to obtain a target image in the image grading method for grading color fundus photos according to the first embodiment of the present application.

Specifically, reference of obtaining an original image and performing enhancement processing on the original image to obtain a target image at foregoing S100 may be made to FIG. 2, which includes following steps.

At S110, clip or scale the original image according to a preset size.

Specifically, the preset size may be set according to an application scene. In this solution, the original image is clipped into a square with a size of 512×512.

At S120, perform normalization processing on the clipped or scaled original image to obtain a processed image.

The normalization processing refers to a process that a series of standard processing and transformations are performed on the image to transform the image into a fixed and standard form. Specifically, in this solution, the clipped or scaled image is uniformly transformed into an image provided with the same average value and variance distribution.

At S130, use a CLAHE (contrast-limited adaptive histogram equalization) algorithm to process the processed image to obtain a target image.

The CLAHE algorithm mainly includes: segmenting the image into blocks, calculating histograms first by taking the block as a unit, then trimming the histograms, and equalizing linear interpolation between the blocks (here, it is necessary to traverse and manipulate each block of the images, which is relatively complicated to process), and finally performing a color filtering and blending operation for layers on the original image. In this embodiment, the contrast limit amplitude, the image is uniformly segmented into rectangular blocks with a size of 8×8, and the histogram of each of blocks is calculated to obtain interpolated values.

At S200, perform color processing on the original image and the target image to obtain a first processed image and a second processed image respectively.

In a convolutional neural network, the image is usually represented by using a RGB (red, green, blue) color space for input, but the RGB color space is closely related to brightness and has a certain limitation. Therefore, in this solution, an HSV (hue, saturation, value) color space is used for input. Specifically, referring to FIG. 3, the step S200 includes following steps.

Figure 3:
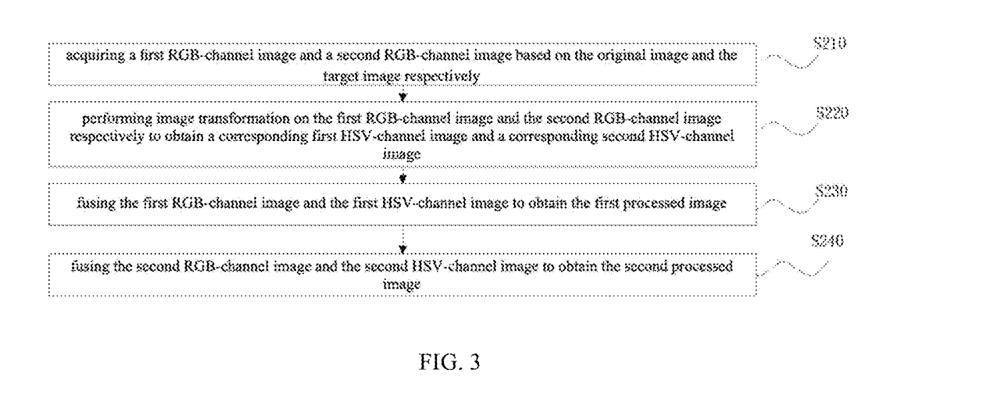
FIG. 3 is a flowchart of performing color processing on the original image and the target image to obtain a first processed image and a second processed image respectively in the image grading method for grading color fundus photos according to the first embodiment of the present application.

At S210, acquire a first RGB-channel image and a second RGB-channel image based on the original image and the target image respectively.

It should be noted that the above RGB channels are: R (red), G (green), and B (blue) respectively, and a variety of colors may be obtained through changes of the three color channels (i.e., R (red), G (green), and B (blue)) and superimpositions thereof.

At S220, perform image transformation on the first RGB-channel image and the second RGB-channel image respectively to obtain a corresponding first HSV-channel image and a corresponding second HSV-channel image.

In this solution, an OPENCV function is used to transform the RGB-channel images into the HSV-channel images, each color of which is represented by one of H (Hue), S (Saturation) and V (Value), and corresponding parameters of the HSV channels are H (Hue), S (Saturation) and V (Value) respectively.

At S230, fuse the first RGB-channel image and the first HSV-channel image to obtain the first processed image.

At S240, fuse the second RGB-channel image and the second HSV-channel image to obtain the second processed image.

In this solution, color space transformations are performed on the original image and the target image, and the original RGB image provided with three channels is fused into an image provided with six channels (i.e., RGB, HSV).

In this solution, a multi-color space (the image provided with six channels, i.e., RGB, HSV) is used as the input of the grading model, which reduces limitation of a traditional color space on brightness sensitivity, and improves generalization performance of the model for multi-device images.

At S300, process the first processed image and the second processed image by using a pre-trained grading model to obtain a target grading result.

In this solution, the grading model includes a first convolutional network, a second convolutional network, and a fusion network. The first convolutional network is used to process the first processed image (i.e., the original image), and the second convolutional network is used to process the second processed image (i.e., the target image). The first convolutional network and the second convolutional network have the same structure and the same processing process, and execute the processing process synchronously.

Figure 4:
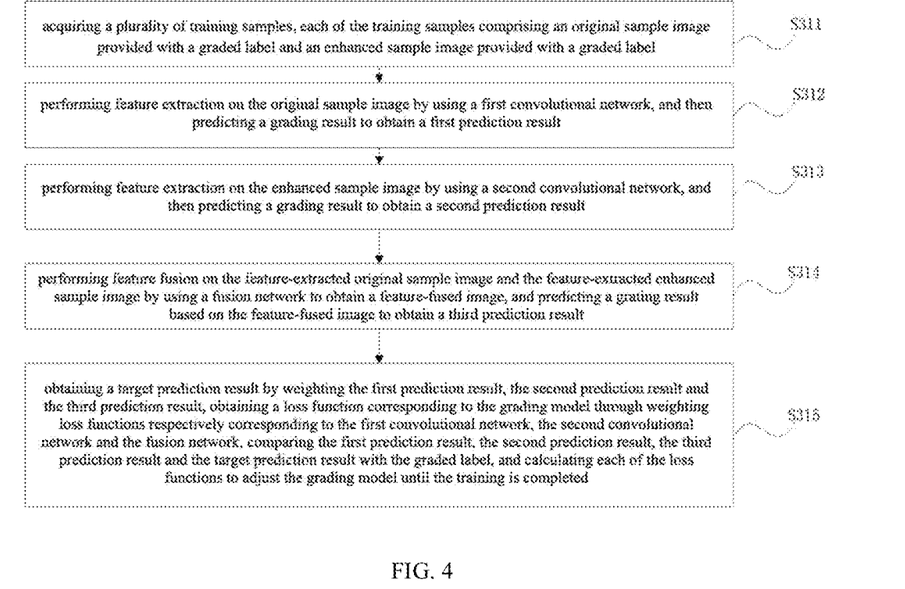
FIG. 4 is a flowchart of training a grading model by using training samples in the image grading method for grading color fundus photos according to the first embodiment of the present application.

Before processing the first processed image and the second processed image by using the pre-trained grading model, the method includes training the grading model by using training samples. Referring to FIG. 4, the training includes following steps.

At S311, acquire a plurality of training samples, each of the training samples includes an original sample image provided with a graded label and an enhanced sample image provided with a graded label.

Here, the graded label includes moderate aged macular degeneration, severe aged macular degeneration, mild-moderate diabetic retinopathy, severe diabetic retinopathy, tigroid fundus, and pathological myopia.

In this solution, the above six types are used as classification labels. The above six types diseases are common diseases. In a subsequent application process, more types of classification labels may also be used for training to improve applicability of the grading model and further increase applicable scenes of the grading method.

At S312, perform feature extraction on the original sample image by using the first convolutional network, and then predict a grading result to obtain a first prediction result.

Figure 5:
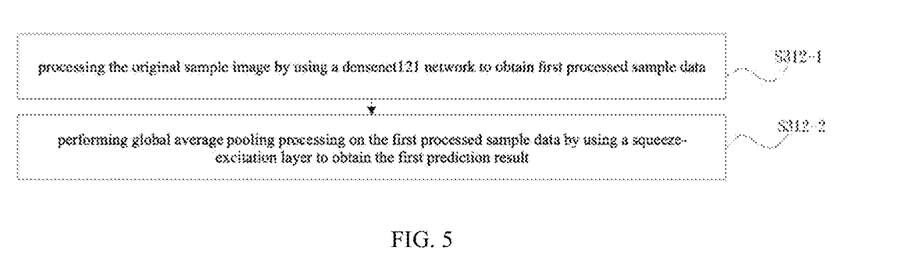
FIG. 5 is a flowchart of predicting, after performing feature extraction on the original image of the samples by using a first convolutional network, a grading result to obtain a first prediction result in the image grading method for grading color fundus photos according to the first embodiment of the present application.

More specifically, reference of performing feature extraction on the original sample image by using the first convolutional network and then predicting a grading result to obtain a first prediction result may be made to FIG. 5, which includes following steps.

At S312-1, process the original sample image by using a densenet121 network to obtain first processed sample data.

In this implementation, the densenet121 network is a classification network, which can achieve a better effect in classification of large data sets through close connection. The advantages of the densenet121 network include: fewer parameters, significantly reduced bandwidth and reduced storage overhead; less calculations; better anti-overfitting performance and generalization performance, and comprehensive use of features with low complexity at a superficial layer. Therefore, it is easier for the densenet121 network to obtain a smooth decision function provided with better generalization performance. In this solution, the densenet121 network is used for classification to realize preliminary grading of the original sample image.

At S312-2, perform global average pooling processing on the first processed sample data by using a squeeze-excitation layer to obtain the first prediction result.

In this implementation, the squeeze-excitation layer may adjust a weight ratio of each channel in terms of global information. A specific implementation is to add a se-block layer after the densenet121 network, so as to further improve the accuracy of the classification result.

At S313, perform feature extraction on the enhanced sample image by using the second convolutional network, and then predict a grading result to obtain a second prediction result.

Figure 6:
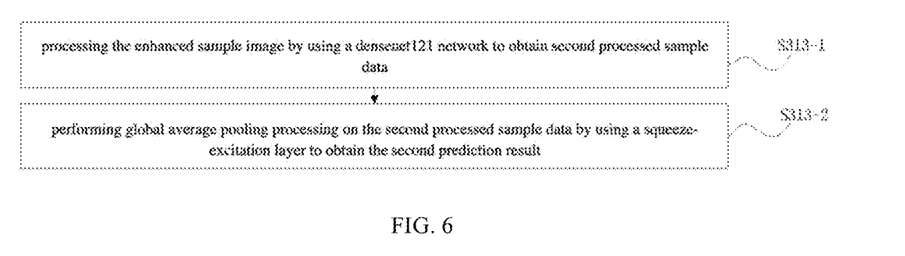
FIG. 6 is a flow chart of predicting, after performing feature extraction on enhanced images of the samples by using a second convolutional network, a grading result to obtain a second prediction result in the image grading method for grading color fundus photos according to the first embodiment of the present application.

Specifically, reference of performing feature extraction on the enhanced sample image by using the second convolutional network and then predicting a grading result to obtain a second prediction result may be made to FIG. 6, which includes following steps.

At S313-1, process the enhanced sample image by using the densenet121 network to obtain second processed sample data.

At S313-2, perform global average pooling processing on the second processed sample data by using the squeeze-excitation layer to obtain the second prediction result.

The steps S313-1 and S313-2 processed by the second convolutional network are the same as the processing procedures of the first convolutional network in the above-mentioned steps S312-1 and S312-2, and the steps S313-1, S313-2 and the steps S312-1 and S312-2 are synchronized processed to perform classification of the original sample image and the enhanced sample image respectively.

At S314, perform feature fusion on the feature-extracted original sample image and the feature-extracted enhanced sample image by using a fusion network to obtain a feature-fused image, and predicting a grading result based on the feature-fused image to obtain a third prediction result.

In this embodiment, the grading is performed after the feature fusion is performed by the fusion network. Specifically, the last convolutional layer of the above two networks (i.e., the first convolutional network and the second convolutional network) is subjected to a concatenate operation and a global average pooling operation, and finally the prediction result is output.

At S315, obtain a target prediction result by weighting the first prediction result, the second prediction result and the third prediction result, obtain a loss function corresponding to the grading model through weighting loss functions respectively corresponding to the first convolutional network, the second convolutional network and the fusion network, compare the first prediction result, the second prediction result, the third prediction result and the target prediction result with the graded label, and calculate each of the loss functions to adjust the grading model until training is completed.

Specifically, the first prediction result, the second prediction result and the third prediction result are weighted and fused with weights of 0.2, 0.2, and 0.6 respectively, and the loss functions respectively corresponding to the first convolutional network, the second convolutional network and the fusion network are also weighted and fused with the weights of 0.2, 0.2, and 0.6 respectively. Through performing the classification prediction on the original image and the enhanced image respectively, and weighting and fusing the loss and the prediction results, the performance and prediction accuracy of the model are improved.

Figure 7:
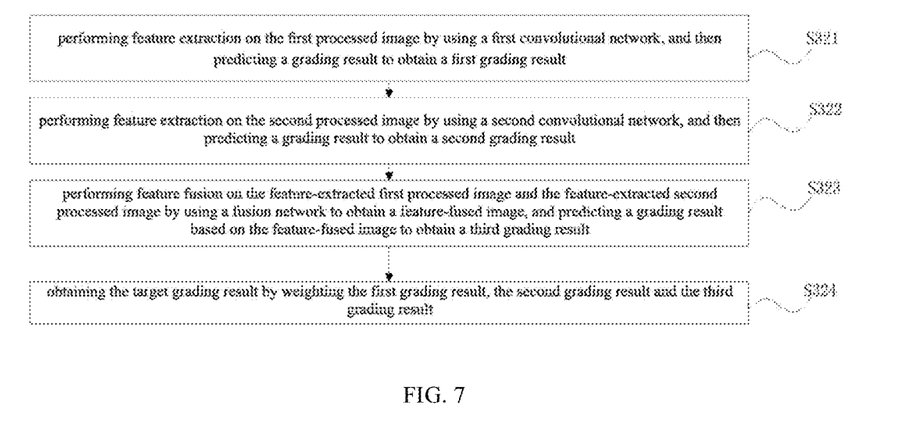
FIG. 7 is a flowchart of processing the first processed image and the second processed image by using a pre-trained grading model to obtain a target grading result in the image grading method for grading color fundus photos according to the first embodiment of the present application.

Specifically, reference of processing the first processed image and the second processed image by using a pre-trained grading model to obtain a target grading result may be made to FIG. 7, which includes following steps.

At S321, perform feature extraction on the first processed image by using the first convolutional network, and then predict a grading result to obtain a first grading result.

Figure 8:
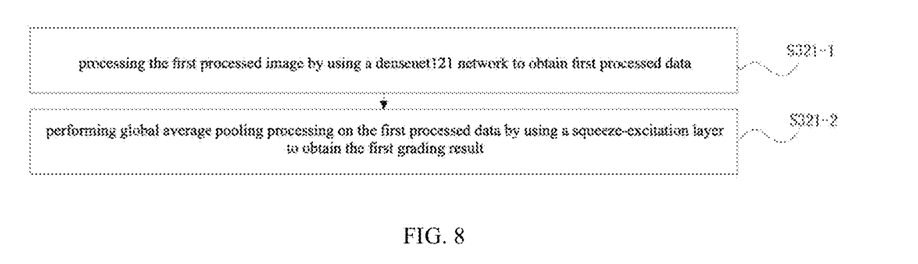
FIG. 8 is a flow chart of predicting, after performing feature extraction on the first processed image by using the first convolutional network, a grading result to obtain a first grading result in the image grading method for grading color fundus photos according to the first embodiment of the present application.

Specifically, reference of performing feature extraction on the first processed image by using the first convolutional network and then predicting a grading result to obtain a first grading result may be made to FIG. 8, which includes following steps of:

at S321-1, processing the first processed image by using a densenet121 network to obtain first processed data;

at S321-2, performing global average pooling processing on the first processed data by using a squeeze-excitation layer to obtain the first grading result.

At S322, perform feature extraction on the second processed image by using the second convolutional network, and then predict a grading result to obtain a second grading result.

Figure 9:
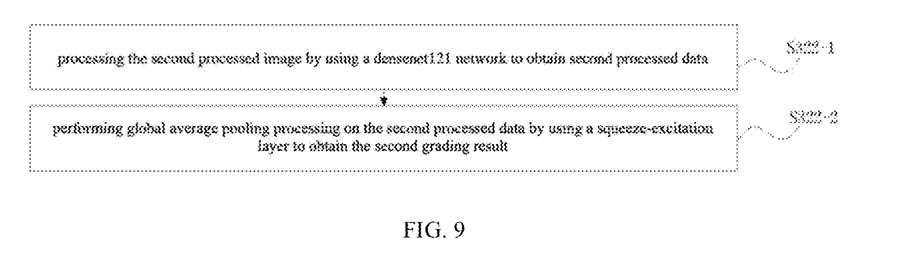
FIG. 9 is a flow chart of predicting, after performing feature extraction on the second processed image by using the second convolutional network, a grading result to obtain a first grading result in the image grading method for grading color fundus photos according to the first embodiment of the present application.

Specifically, reference of performing feature extraction on the second processed image by using the second convolutional network and then predicting a grading result to obtain a second grading result may be made to FIG. 9, which includes:

at S322-1, processing the second processed image by using the densenet121 network to obtain second processed data;

at S322-2, performing global average pooling processing on the second processed data by using the squeeze-excitation layer to obtain the second grading result.

In this solution, the processing processes of the above S321 and S322 are the same as that of S312 and S313 in the above training process. The first convolutional network and the second convolutional network are respectively used to perform grading prediction on the first processed image (the original image after color transformation) and the second processed image (the target image after color transformation), and the feature fusion that is added with an attention module is achieved through the squeeze-excitation layer.

At S323, perform feature fusion on the feature-extracted first processed image and the feature-extracted second processed image by using the fusion network to obtain a feature-fused image, and predict a grading result based on the feature-fused image to obtain a third grading result.

In this solution, the processing process of the fusion network at S323 and are consistent with that of the fusion network in the training process, and the prediction is performed at a full-image scale through the fused features, thereby reducing prediction errors caused by inaccurate segmentation and positioning, and in turn improving the accuracy of the grading results.

At S324, obtain the target grading result by weighting the first grading result, the second grading result and the third grading result.

In this solution, the grading prediction is performed on the original image and the enhanced image (that is, the target image) respectively, and the first grading result, the second grading result and the third grading result are weighted and fused with the weights of 0.2, 0.2 and 0.6, therefore the performance and prediction accuracy of the model is further improved; at the same time, the target grading result includes, but is not limited to, 6 common fundus diseases shown in the color photo, namely mild-moderate aged macular degeneration, severe aged macular degeneration, mild-moderate diabetic retinopathy, severe diabetic retinopathy, tigroid fundus and pathological myopia, and the automatic grading is achieved through the above grading model, which further reduces the problems of large workload and low efficiency caused by manual analysis and can automatically screen out the color photo of the diseased fundus, thereby achieving the effect of pre-screening and improving the work efficiency.

In this solution, the original image, target image, and target grading result may also be uploaded to a blockchain, so that the above-mentioned data may be obtained from the blockchain for reference or as a sample, thereby ensuring safety, fairness and transparency for a user. A user device may download summary information from the blockchain to verify whether a priority list has been tampered. The blockchain referred to in the present application is a new application mode of a computer technology such as distributed data storage, point-to-point transmission, consensus mechanism, and encryption algorithm. The blockchain is essentially a decentralized database, and is a series of data blocks generated by a method associated with cryptology. Each of the data blocks contains a batch of network transaction information to verify validity of the information (anti-counterfeiting) and generate a next block. The blockchain may include a underlying platform, a platform product service layer, and an application service layer of the blockchain.

Second Embodiment

Figure 10:
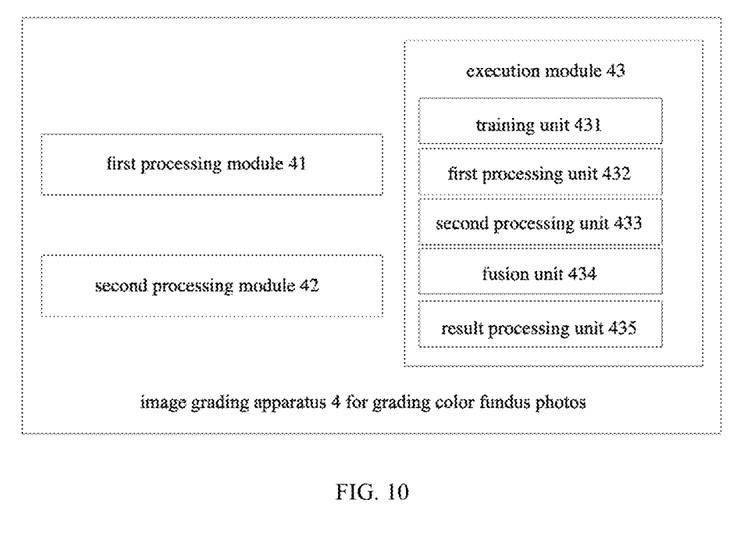
FIG. 10 is a schematic diagram of program modules of an image grading apparatus for grading color fundus photos according to a second embodiment of the present application.

Please refer to FIG. 10, an image grading apparatus 4 for grading color fundus photos in this embodiment includes:
a first processing module 41 configured to obtain an original image and perform enhancement processing on the original image to obtain a target image,
here specifically, the enhancement processing includes clipping or scaling the original image according to a preset size, performing normalization processing on the clipped original image, and using a CLAHE algorithm for processing, other processing means capable of achieving the enhancement on the original image may also be used;
a second processing module 42 configured to perform color processing on the original image and the target image to obtain a first processed image and a second processed image respectively,
here specifically, the color processing includes transforming a RGB-channel image into an HSV-channel image through an OPENCV function, and fusing the RGB-channel image with the HSV-channel image to finally obtain a six-channel original image and a six-channel target image as the obtained first processed image and second processed image respectively;
an execution module 43 configured to process the first processed image and the second processed image by using a pre-trained grading model to obtain a target grading result.

Specifically, the execution module 43 further includes:
a training unit 431 configured to pre-train the grading model by using training samples;
a first processing unit 432 configured to perform feature extraction on the first processed image by using a first convolutional network and then predict a grading result to obtain a first grading result,
here specifically, the first convolutional network includes a densenet121 network and a squeeze-excitation layer added to an output layer of the densenet121 network, such that a global average pooling operation is performed on an output of the first convolutional network;
a second processing unit 433 configured to perform feature extraction on the second processed image by using a second convolutional network and then predict a grading result to obtain a second grading result,
here specifically, a structure and processing processes of the second convolutional network are consistent with that of the first convolutional network in the first processing unit 432;
a fusion unit 434 configured to perform feature fusion on the feature-extracted first processed image and the feature-extracted second processed image by using a fusion network to obtain a feature-fused image and predict a grading result based on the feature-fused image to obtain a third grading result,
here specifically, a concatenate operation and a global average pooling operation are performed on a last convolutional layer of the above two networks (i.e., the first convolutional network and the second convolutional network) to finally output the third grading result;
a result processing unit 435 configured to obtain the target grading result by weighting the first grading result, the second grading result and the third grading result.

Specifically, the result processing unit weights the first grading result, the second grading result and the third grading result with weights of 0.2, 0.2 and 0.6, and the target grading result includes, but is not limited to, 6 common fundus diseases shown in the color photo, namely mild-moderate aged macular degeneration, severe aged macular degeneration, mild-moderate diabetic retinopathy, severe diabetic retinopathy, tigroid fundus and pathological myopia respectively.

This technical solution is based on a prediction model in intelligent decision-making, which performs enhancement processing such as cropping, scaling, normalization, contrast algorithm etc. on the original image by the first processing module to obtain the enhanced original image as the target image, and performs color space processing (i.e., processes the RGB-channel image to obtain an image provided with 6 channels of RGB and HSV) on the original image and the target image by the second processing module to obtain the corresponding first processed image and second processed image, and finally performs grading and prediction on the first processed image and the second processed image by using the trained grading model through the execution module to obtain the target grading result. In this solution, the first processed image and the second processed image in the multi-color space are as input of the grading model, and then the grading model processes to realize classification and grading of common fundus diseases shown in the color photos, which can automatically screen out the color photo of the diseased fundus and achieve an effect of pre-screening and improvement of the work efficiency, thereby effectively solving the problems that the color fundus photo identification in the prior art mostly depends on the experience of doctors, that only some diseases can be automatically identified based on the color fundus photos, and that there is a lack of a method for automatically screening out color fundus photos suitable for common diseases.

In this solution, the processing process of the execution module also includes: using the first convolutional network of the first processing unit and the second convolutional network of the second processing unit to perform grading prediction on the first processed image and the second processed image respectively; then performing grading prediction by the fusion unit after feature fusion is performed on the first processed image and the second processed image; finally fusing and weighting by the result processing unit based on the grading results obtained from the grading predictions to obtain the target grading result, which reduces prediction errors due to inaccurate segmentation and positioning; at the same time, performing classification and prediction on the original image and the enhanced image (i.e., the target image), and weighting and fusing the loss and prediction results, which further improves the performance and prediction accuracy of the model.

Third Embodiment

Figure 11:
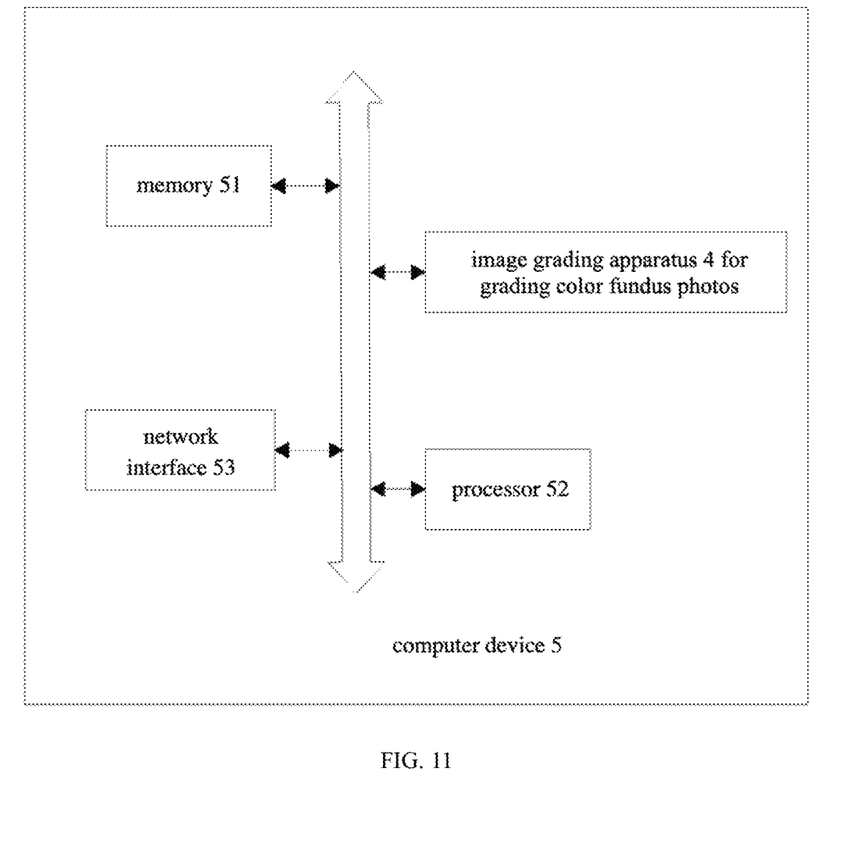
FIG. 11 is a structural schematic diagram of hardware of a computer device according to a third embodiment of the present application including a computer device.

In order to achieve the above-mentioned objectives, the present application further provides a computer device 5, which may include multiple computer devices 5. The components of the image grading apparatus 4 for grading color fundus photos in the second embodiment may be distributed in different computer devices 5. The computer device 5 may be a smart phone, a tablet, a laptop, a desktop computer, a rack server, a blade server, a tower server, or a cabinet server (including an independent server, or a server cluster including a plurality of servers) etc. that executes a program. As shown in FIG. 11, the computer device of this embodiment at least includes, but is not limited to: a memory 51, a processor 52, a network interface 53, and an image grading apparatus 4 for grading color fundus photos that may be communicably connected to each other through a system bus. It should be pointed out that FIG. 11 only shows a computer device provided with components, but it should be understood that it is not required to implement all the illustrated components, and more or fewer components may be implemented instead.

In this embodiment, the memory 51 includes at least one type of computer-readable storage medium. The readable storage medium includes a flash memory, a hard disk, a multimedia card, a card-type memory (for example, SD or DX memory, etc.), a RAM (random access memory), a SRAM (static random access memory), a ROM (read-only memory), an EEPROM (electrically erasable programmable read-only memory), a PROM (programmable read-only memory), a magnetic memory, a magnetic disk, or an optical disk, etc. In some embodiments, the memory 51 may be an internal storage unit of the computer device, such as a hard disk or memory of the computer device. In other embodiments, the memory 51 may also be an external storage device of the computer device, for example, a plug-in hard disk, a SMC (smart memory card), a SD (secure digital) card, or a flash card etc. equipped on the computer device. Of course, the memory 51 may also include both an internal storage unit of the computer device and an external storage device thereof. In this embodiment, the memory 51 is generally used to store an operating system and various application software installed in the computer device, such as a program code of the image grading method for grading color fundus photos in the first embodiment, and the like. In addition, the memory 51 may also be used to temporarily store various types of data that have been output or will be output.

The processor 52, in some embodiments, may be a CPU (central processing unit), a controller, a microcontroller, a microprocessor, or other data processing chip. The processor 52 is generally used to control the overall operations of the computer device. In this embodiment, the processor 52 is used to run the program code or processing data stored in the memory 51, for example, used to run an image grading apparatus 4 for grading color fundus photos, so as to implement the image grading method for grading color fundus photos in the first embodiment.

The network interface 53 may include a wireless network interface or a wired network interface, and the network interface 53 is generally used to establish a communication connection between the computer device 5 and another computer devices 5. For example, the network interface 53 is used to connect the computer device 5 with an external terminal through a network, and establish a data transmission channel and a communication connection between the computer device 5 and the external terminal. The network may be a wireless or wired network such as an intranet, an internet, a GSM (global system of mobile communication), a WCDMA (wideband code division multiple access), a 4G network, a 5G Network, Bluetooth, or Wi-Fi etc.

It should be pointed out that FIG. 11 only shows the computer device 5 provided with components 51, 52 and 53, but it should be understood that it is not required to implement all the components as shown in the figure, and more or fewer components may be implemented instead.

In this embodiment, the image grading apparatus 4 for grading color fundus photos stored in the memory 51 may further be divided into one or more program modules, and the one or more program modules are stored in the memory 51 and are executed by a plurality of processors (the processor 52 in this embodiment) to complete the present application.

Fourth Embodiment

In order to achieve the above objectives, the present application further provides a computer-readable storage medium. The computer-readable storage medium may be non-volatile or volatile, and includes a plurality of storage media, such as a flash memory, a hard disk, a multimedia card, a card-type memory (for example, SD or DX memory, etc.), a RAM (random access memory), a SRAM (static random access memory), a ROM (read-only memory), an EEPROM (electrically erasable programmable read-only memory), a PROM (programmable read-only memory), a magnetic memory, a magnetic disk, an optical disk, a server, and an APP application store etc. A computer program is stored on the computer-readable storage medium, and the program, when executed by the processor 52, implements a corresponding function. The computer-readable storage medium in this embodiment is used to store an image grading apparatus for grading color fundus photos, which, when executed by the processor 52, implements the image grading method for grading color fundus photos in the first embodiment.

The serial numbers of the foregoing embodiments of the present application are only for description, and do not represent superiority or inferiority of the embodiments.

Through the description of the above embodiments, those skilled in the art can clearly understand that the methods in the above embodiments can be implemented by means of software together with a necessary general hardware platform, of course, may also be implemented by means of hardware, but the former is a better implementation in many cases.

The above embodiments are only preferred embodiments of the present application, and do not thereby limit the patent scope of the present application. Any equivalent structure or equivalent process transformation made by using the content of the description and drawings of the present application, or any direct or indirect application in other related technical fields, are included in the patent protection scope of the present application.

What is claimed is:

1. An image grading method for grading color fundus photos, comprising:
   obtaining an original image, and performing enhancement processing on the original image to obtain a target image;
   performing color processing on the original image and the target image to obtain a first processed image and a second processed image respectively;
   processing the first processed image and the second processed image by using a pre-trained grading model to obtain a target grading result, the pre-trained grading model comprises a first convolutional network, a second convolutional network, and a fusion network, the first convolutional network being used to process the first processed image, and the second convolutional network is used to process the second processed image;
   wherein, the processing the first processed image and the second processed image by using a pre-trained grading model to obtain a target grading result comprises:
   performing feature extraction on the first processed image by using the first convolutional network, and then predicting a grading result to obtain a first grading result;
   performing feature extraction on the second processed image by using the second convolutional network, and then predicting a grading result to obtain a second grading result;
   performing feature fusion on the feature-extracted first processed image and the feature-extracted second processed image by using the fusion network to obtain a feature-fused image, and predicting a grading result based on the feature-fused image to obtain a third grading result;
   obtaining the target grading result by weighting the first grading result, the second grading result and the third grading result.

2. The image grading method for grading color fundus photos according to claim 1, wherein, the performing enhancement processing on the original image to obtain a target image comprises:
   clipping or scaling the original image according to a preset size;
   performing normalization processing on the clipped or scaled original image to obtain a processed image;
   processing the processed image by using a CLAHE algorithm to obtain the target image.

3. The image grading method for grading color fundus photos according to claim 1, wherein, the performing color processing on the original image and the target image to obtain a first processed image and a second processed image respectively comprises:
   acquiring a first RGB-channel image provided with three channels and a second RGB-channel image provided with three channels based on the original image and the target image respectively;
   performing image transformation on the first RGB-channel image provided with three channels and the second RGB-channel image provided with three channels respectively to obtain a corresponding first HSV-channel image provided with three channels and a corresponding second HSV-channel image provided with three channels;
   fusing the first RGB-channel image and the first HSV-channel image to obtain the first processed image;
   fusing the second RGB-channel image and the second HSV-channel image to obtain the second processed image.

4. The image grading method for grading color fundus photos according to claim 1, wherein, before processing the first processed image and the second processed image by using a pre-trained grading model, the image grading method comprises training the grading model by using training samples, and the training comprises:
   acquiring a plurality of training samples, each of the training samples comprising an original sample image provided with a graded label and an enhanced sample image provided with a graded label, wherein the graded label comprises moderate aged macular degeneration, severe aged macular degeneration, mild-moderate diabetic retinopathy, severe diabetic retinopathy, tigroid fundus, and pathological myopia;
   performing feature extraction on the original sample image by using the first convolutional network, and then predicting a grading result to obtain a first prediction result;
   performing feature extraction on the enhanced sample image by using the second convolutional network, and then predicting a grading result to obtain a second prediction result;
   performing feature fusion on the feature-extracted original sample image and the feature-extracted enhanced sample image by using the fusion network to obtain a feature-fused image, and predicting a grading result based on the feature-fused image to obtain a third prediction result;
   obtaining a target prediction result by weighting the first prediction result, the second prediction result and the third prediction result, obtaining a loss function corresponding to the grading model through weighting loss functions respectively corresponding to the first convolutional network, the second convolutional network and the fusion network, comparing the first prediction result, the second prediction result, the third prediction result and the target prediction result with the graded label, and calculating each of the loss functions to adjust the grading model until the training is completed.

5. The image grading method for grading color fundus photos according to claim 1, wherein, the performing feature extraction on the first processed image by using the first convolutional network and then predicting a grading result to obtain a first grading result comprises:
   processing the first processed image by using a densenet121 network to obtain first processed data;
   performing global average pooling processing on the first processed data by using a squeeze-excitation layer to obtain the first grading result.

6. The image grading method for grading color fundus photos according to claim 1, wherein, the performing feature extraction on the second processed image by using the second convolutional network and then predicting a grading result to obtain a second grading result comprises:
processing the second processed image by using a densenet121 network to obtain second processed data;
performing global average pooling processing on the second processed data by using a squeeze-excitation layer to obtain the second grading result.

7. An image grading apparatus for grading color fundus photos, comprising:
a first processing module configured to obtain an original image and perform enhancement processing on the original image to obtain a target image,
a second processing module configured to perform color processing on the original image and the target image to obtain a first processed image and a second processed image respectively,
an execution module configured to process the first processed image and the second processed image by using a pre-trained grading model to obtain a target grading result, the pre-trained grading model comprises a first convolutional network, a second convolutional network, and a fusion network, the first convolutional network being used to process the first processed image, and the second convolutional network is used to process the second processed image;
wherein, the execution module performed the following steps to processes the first processed image and the second processed image using the pre-trained grading model to obtain the target grading result:
performing feature extraction on the first processed image by using the first convolutional network, and then predicting a grading result to obtain a first grading result;
performing feature extraction on the second processed image by using the second convolutional network, and then predicting a grading result to obtain a second grading result;
performing feature fusion on the feature-extracted first processed image and the feature-extracted second processed image by using the fusion network to obtain a feature-fused image, and predicting a grading result based on the feature-fused image to obtain a third grading result; and
obtaining the target grading result by weighting the first grading result, the second grading result and the third grading result.

8. The image grading apparatus for grading color fundus photos according to claim 7, wherein, the first processing module is configured to: clip or scale the original image according to a preset size; perform normalization processing on the clipped or scaled original image to obtain a processed image; and process the processed image by using a CLAHE algorithm to obtain the target image.

9. The image grading apparatus for grading color fundus photos according to claim 7, wherein, the second processing module is configured to: acquire a first RGB-channel image provided with three channels and a second RGB-channel image provided with three channels based on the original image and the target image respectively; perform image transformation on the first RGB-channel image provided with three channels and the second RGB-channel image provided with three channels respectively to obtain a corresponding first HSV-channel image provided with three channels and a corresponding second HSV-channel image provided with three channels; fuse the first RGB-channel image and the first HSV-channel image to obtain the first processed image; and fuse the second RGB-channel image and the second HSV-channel image to obtain the second processed image.

10. A computer device, comprising a non-transitory computer readable-medium, a processor and a computer program stored on the non-transitory computer readable-medium and capable of being executed on the processor, wherein the processor, when executing the computer program, implements following steps of an image grading method for grading color fundus photos:
obtaining an original image, and performing enhancement processing on the original image to obtain a target image;
performing color processing on the original image and the target image to obtain a first processed image and a second processed image respectively;
processing the first processed image and the second processed image by using a pre-trained grading model to obtain a target grading result, the pre-trained grading model comprises a first convolutional network, a second convolutional network, and a fusion network, the first convolutional network being used to process the first processed image, and the second convolutional network is used to process the second processed image;
wherein, the processing the first processed image and the second processed image by using a pre-trained grading model to obtain a target grading result comprises:
performing feature extraction on the first processed image by using the first convolutional network, and then predicting a grading result to obtain a first grading result;
performing feature extraction on the second processed image by using the second convolutional network, and then predicting a grading result to obtain a second grading result;
performing feature fusion on the feature-extracted first processed image and the feature-extracted second processed image by using the fusion network to obtain a feature-fused image, and predicting a grading result based on the feature-fused image to obtain a third grading result; and
obtaining the target grading result by weighting the first grading result, the second grading result and the third grading result.

11. The computer device according to claim 10, wherein, the performing enhancement processing on the original image to obtain a target image comprises:
clipping or scaling the original image according to a preset size;
performing normalization processing on the clipped or scaled original image to obtain a processed image;
processing the processed image by using a CLAHE algorithm to obtain the target image.

12. The computer device according to claim 10, wherein, the performing color processing on the original image and the target image to obtain a first processed image and a second processed image respectively comprises:
acquiring a first RGB-channel image provided with three channels and a second RGB-channel image provided with three channels based on the original image and the target image respectively;
performing image transformation on the first RGB-channel image provided with three channels and the second RGB-channel image provided with three channels respectively to obtain a corresponding first HSV-channel image provided with three channels and a corresponding second HSV-channel image provided with three channels;

fusing the first RGB-channel image and the first HSV-channel image to obtain the first processed image;

fusing the second RGB-channel image and the second HSV-channel image to obtain the second processed image.

13. The computer device according to claim 10, wherein, the performing feature extraction on the first processed image by using the first convolutional network and then predicting a grading result to obtain a first grading result comprises:

processing the first processed image by using a densenet121 network to obtain first processed data;

performing global average pooling processing on the first processed data by using a squeeze-excitation layer to obtain the first grading result.

14. The computer device according to claim 10, wherein, the performing feature extraction on the second processed image by using the second convolutional network and then predicting a grading result to obtain a second grading result comprises:

processing the second processed image by using a densenet121 network to obtain second processed data;

performing global average pooling processing on the second processed data by using a squeeze-excitation layer to obtain the second grading result.

15. The computer device according to claim 10, wherein, before processing the first processed image and the second processed image by using the pre-trained grading model, the image grading method comprises training the grading model by using training samples, and the training comprises:

acquiring a plurality of training samples, each of the training samples comprising an original sample image provided with a graded label and an enhanced sample image provided with a graded label, wherein the graded label comprises moderate aged macular degeneration, severe aged macular degeneration, mild-moderate diabetic retinopathy, severe diabetic retinopathy, tigroid fundus, and pathological myopia;

performing feature extraction on the original sample image by using the first convolutional network, and then predicting a grading result to obtain a first prediction result;

performing feature extraction on the enhanced sample image by using the second convolutional network, and then predicting a grading result to obtain a second prediction result;

performing feature fusion on the feature-extracted original sample image and the feature-extracted enhanced sample image by using the fusion network to obtain a feature-fused image, and predicting a grating result based on the feature-fused image to obtain a third prediction result;

obtaining a target prediction result by weighting the first prediction result, the second prediction result and the third prediction result, obtaining a loss function corresponding to the grading model through weighting loss functions respectively corresponding to the first convolutional network, the second convolutional network and the fusion network, comparing the first prediction result, the second prediction result, the third prediction result and the target prediction result with the graded label, and calculating each of the loss functions to adjust the grading model until the training is completed.

16. The image grading apparatus for grading color fundus photos according to claim 7, wherein, both the first convolutional network and the second convolutional network include a densenet121 network and a squeeze-excitation layer added to an output layer of the densenet121 network respectively, such that a global average pooling operation is performed on an output of the first convolutional network and an output of the second convolutional network.

17. The image grading apparatus for grading color fundus photos according to claim 7, wherein, weights of weighting the first grading result, the second grading result and the third grading result are 0.2, 0.2 and 0.6 respectively.

* * * * *